(12) United States Patent
Soza et al.

(10) Patent No.: US 9,460,534 B2
(45) Date of Patent: Oct. 4, 2016

(54) LABELING A RIB CAGE BY PLACING A LABEL BASED ON A CENTER POINT AND POSITION OF A RIB

(71) Applicant: SIEMENS AKTIENGESELLSCHAFT, Munich (DE)

(72) Inventors: Grzegorz Soza, Heroldsberg (DE); Andreas Wimmer, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 317 days.

(21) Appl. No.: 14/077,289

(22) Filed: Nov. 12, 2013

(65) Prior Publication Data

US 2015/0135055 A1 May 14, 2015

(51) Int. Cl.
```
G06T 11/60     (2006.01)
G06T 7/00      (2006.01)
A61B 6/03      (2006.01)
A61B 5/00      (2006.01)
```

(52) U.S. Cl.
CPC ............ G06T 11/60 (2013.01); G06T 7/0081 (2013.01); *A61B 5/4836* (2013.01); *A61B 6/032* (2013.01); *G06T 7/0012* (2013.01); *G06T 7/0083* (2013.01); *G06T 2207/10072* (2013.01); *G06T 2207/10081* (2013.01); *G06T 2207/10116* (2013.01); *G06T 2207/30004* (2013.01); *G06T 2207/30008* (2013.01)

(58) Field of Classification Search
CPC ............ G06T 2210/41; G06T 7/0012; G06T 2207/30008; G06T 2207/10116; G06T 2207/10081; G06T 2207/10072; G06T 11/60; G06F 17/241; A61B 6/032; A61B 5/4836
See application file for complete search history.

(56) References Cited

U.S. PATENT DOCUMENTS

| | | | |
|---|---|---|---|
| 8,963,829 B2* | 2/2015 | Lee | G06F 3/017 345/156 |
| 2005/0234448 A1 | 10/2005 | McCarthy | |
| 2007/0130517 A1* | 6/2007 | Wu | G06F 17/30719 715/209 |
| 2007/0249910 A1 | 10/2007 | Kiraly | |
| 2008/0066016 A1* | 3/2008 | Dowdy | G06F 17/30775 715/854 |

(Continued)

OTHER PUBLICATIONS

Tracing Based Segmentation for the Labeling of Individual Rib Structures in Chest CT Volume Data, Hong, Chen, all pages, 2004 copyright.*

(Continued)

*Primary Examiner* — Cesar Paula
*Assistant Examiner* — Benjamin Norris
(74) *Attorney, Agent, or Firm* — Harness, Dickey & Pierce, P.L.C.

(57) ABSTRACT

In at least one embodiment of the invention, a method of rib labeling for 2D images is disclosed. In at least one embodiment a corresponding computation unit, a system including a computation unit and a displaying unit, a medical imaging device, and a computer program are also disclosed. According to a first embodiment of the invention, the method of rib labeling includes receiving a plurality of 2D images representing cross sections of a rib cage, each 2D image comprising cross sections of a plurality of ribs; and generating an anatomical label for each of the ribs in each of the 2D images, each anatomical label being placed radially outside the rib cage. Each anatomical label is placed in the vicinity of the cross section of the respective rib to provide a simple identification of the respective rib.

18 Claims, 4 Drawing Sheets

(56) References Cited

U.S. PATENT DOCUMENTS

| | | |
|---|---|---|
| 2012/0106810 A1 | 5/2012 | Alvino |
| 2012/0159391 A1* | 6/2012 | Berry .................. A61B 5/4824 715/823 |
| 2013/0070996 A1 | 3/2013 | Comaniciu |
| 2013/0077841 A1 | 3/2013 | Comaniciu |
| 2013/0101197 A1* | 4/2013 | Kaftan .................. G06T 5/00 382/131 |
| 2013/0136322 A1 | 5/2013 | Dewan |

OTHER PUBLICATIONS

A learning Based Deformable Template Matching Method for Automatic Rib Centerline Extraction and Labeling in CT images, Wu, Dijia, all pages, 2012 Copyright.*

U.S. Appl. No. 14/077,293, filed Nov. 12, 2013.

U.S. Notice of Allowance for corresponding U.S. Appl. No. 14/077,293 mailed Jul. 15, 2015.

* cited by examiner

LABELING A RIB CAGE BY PLACING A LABEL BASED ON A CENTER POINT AND POSITION OF A RIB

APPLICATION STATEMENT

The present application with U.S. application entitled "2D Visualization For Rib Analysis" to Gnanamani et al. (Ser. No. 14/077,293 issued as U.S. Pat. No. 9,189,847) filed on even date herewith on Nov. 12, 2013, the entire contents of which are hereby incorporated herein by reference.

FIELD

The present invention relates generally to the field of medical imaging, and, more particularly, to rib labeling for two-dimensional ("2D") images.

BACKGROUND

High-resolution computed tomography ("CT") volumes of the chest are commonly used to diagnose abnormalities in the ribs. Current technology provides CT volumes of the chest with up to several hundred 2D slices. Thorough evaluation of thoracic CT scans frequently requires physicians to identify and track the individual ribs structures in the volume data. This can be a tedious task as the ribs occupy multiple slices within the data. More precisely, the ribs typically cross through the axial planes at an oblique angle, thereby making their examination even more problematic. To analyze the CT volumes, the radiologist must scroll through all slices, and view the contents of the ribs while tracking the ribs through each slice. Moreover, given a rib in an arbitrary slice, the radiologist must scroll up and down to determine the number of the rib.

SUMMARY

In at least one embodiment of the invention, a method of rib labeling for 2D images is disclosed. In at least one embodiment a corresponding computation unit, a system including a computation unit and a displaying unit, a medical imaging device, and a computer program are also disclosed. The 2D images are previously recorded by use of a medical imaging device, e.g. by use of a magnetic resonance imaging ("MRI") system, an X-ray system, a positron emission tomography ("PET") system or any other medical imaging device. In a preferable embodiment of the invention the 3D image data is previously recorded by way of a CT system. In further embodiments of the inventions contrast agents such as iodide-containing solution or radioactive tracers can be employed for recording measuring data. It is understood, that the term "2D images" refer to reconstructed images.

According to a first embodiment of the invention, the method of rib labeling comprises receiving a plurality of 2D images representing cross sections of a rib cage, each 2D image comprising cross sections of a plurality of ribs, and generating an anatomical label for each of the ribs in each of the 2D images, each anatomical label being placed radially outside the rib cage. Each anatomical label is placed in the vicinity of the cross section of the respective rib to provide a simple identification of the respective rib. By placing the ribs radially outside the rib cage an overlap between an anatomical label and the respective cross sections of a rib is prevented. Thus the invention allows labeling ribs without occluding valuable image information.

At least one embodiment of the invention can also be realized as a computation unit for rib labeling, comprising a program memory for storage of program code, the program code being present in the program memory and carrying out, when executed, receiving a plurality of two-dimensional images representing cross sections of a rib cage, each two-dimensional image comprising cross sections of a plurality of ribs, generating an anatomical label for each of the ribs in each of the two-dimensional images, each anatomical label being placed radially outside the rib cage. At least one embodiment of the invention can also be realized as medical imaging device comprising such a computation unit.

At least one embodiment of the invention can also be realized as a non-transitory computer readable medium including program segments for, when executed on a computer device, causing the computer device to carry out the inventive method. The invention can also be realized as a computer program product, comprising program code segments of a computer program stored on a non-transitory computer-readable data carrier to execute the inventive method when the computer program is executed on a computer.

At least one embodiment of the invention can also be realized as a system including a computation unit for rib labeling and a displaying unit for visualization of the rib labeling, wherein the computation unit comprises a program memory for storage of program code, the program code being present in the program memory and carrying out, when executed, receiving a plurality of two-dimensional images representing cross sections of a rib cage, each two-dimensional image comprising cross sections of a plurality of ribs, generating an anatomical label for each of the ribs in each of the two-dimensional images, each anatomical label being placed radially outside the rib cage. Such a computation unit can also be configured to obtain instructions via a user-interface. According to another embodiment of the invention, the computation unit is acting as a server and the displaying unit is acting as a client, wherein the displaying unit is configured to receive the labeled 2D image from the computation unit via a network connection.

BRIEF DESCRIPTION OF THE DRAWINGS

The invention is explained in greater detail below on the basis of an example embodiment. Wherein.

DETAILED DESCRIPTION OF THE EXAMPLE EMBODIMENTS

Figure 1:
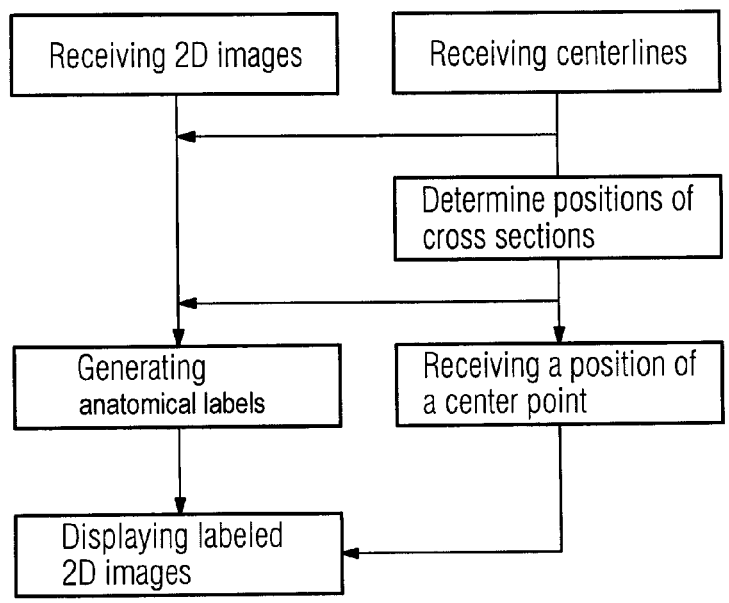
FIG. 1: shows a flowchart of various example embodiments of the inventive method.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to a first embodiment of the invention, the method of rib labeling comprises receiving a plurality of 2D images representing cross sections of a rib cage, each 2D image comprising cross sections of a plurality of ribs, and generating an anatomical label for each of the ribs in each of the 2D images, each anatomical label being placed radially outside the rib cage. Each anatomical label is placed in the vicinity of the cross section of the respective rib to provide a simple identification of the respective rib. By placing the ribs radially outside the rib cage an overlap between an anatomical label and the respective cross sections of a rib is prevented. Thus the invention allows labeling ribs without occluding valuable image information.

According to an embodiment of the invention, the method of rib labeling comprises receiving a centerline of each of the plurality of ribs, each anatomical label being placed based on a position of the centerline of the respective rib. The centerline of a rib describes the orientation and position of the respective rib with high precision in three-dimensional space. Furthermore the centerline of a rib can be used to determine the position of the cross section of the respective rib. Thus this aspect of the invention leads to a particularly precise location of the anatomical labels.

According to an embodiment of the invention, the method of rib labeling comprises receiving a position of a center point of the rib cage, each anatomical label being placed based on the distance between the position of the center point and of a position of the cross section of the respective rib. This embodiment of the invention can be realized by placing each anatomical label along the direction of the distance vector and yields, thus, a very regular and intuitive placement of the anatomical labels.

According to an embodiment of the invention, the method of rib labeling comprises receiving a centerline of each of the plurality of ribs, and determining the position of the cross section of the respective rib based on the position of the centerline of the respective rib. This embodiment of the invention allows determining the position of the cross section of a rib in a very precise and well defined manner. As a consequence the anatomical labels can be placed in a very precise and well defined manner, too.

According to an embodiment of the invention, each anatomical label is placed in a variable distance from the position of the cross section of the respective rib, wherein the variable distance depends on the distance between the position of the center point and of the position of the cross section of the respective rib. According to another embodiment of the invention, the method of rib labeling each anatomical label is placed in the same, fixed distance from the position of the cross section of the respective rib. Both aspects of the invention lead to a very regular placement of the anatomical labels and allow a very fast and simple identification of an individual rib by its anatomical label.

According to an embodiment of the invention, the 2D images are given by multiplanar reconstructions or by curved planar reconstructions. These reconstructions provide particularly relevant image information for diagnostic purposes.

According to an embodiment of the invention, the method comprises displaying simultaneously at least two different labeled 2D images, wherein the at least two labeled 2D images differ in perspective. This aspect allows looking at cross sections of a rib cage with consistently labeled ribs from different perspectives. Visual analysis of ribs becomes thus faster and more reliable.

According to an embodiment of the invention, the at least two labeled 2D images differ in the orientation of the sectional planes. This aspect of the invention allows viewing labeled cross sections of the rib cages in different sectional planes such as sagittal, transverse or frontal.

Figure 6:
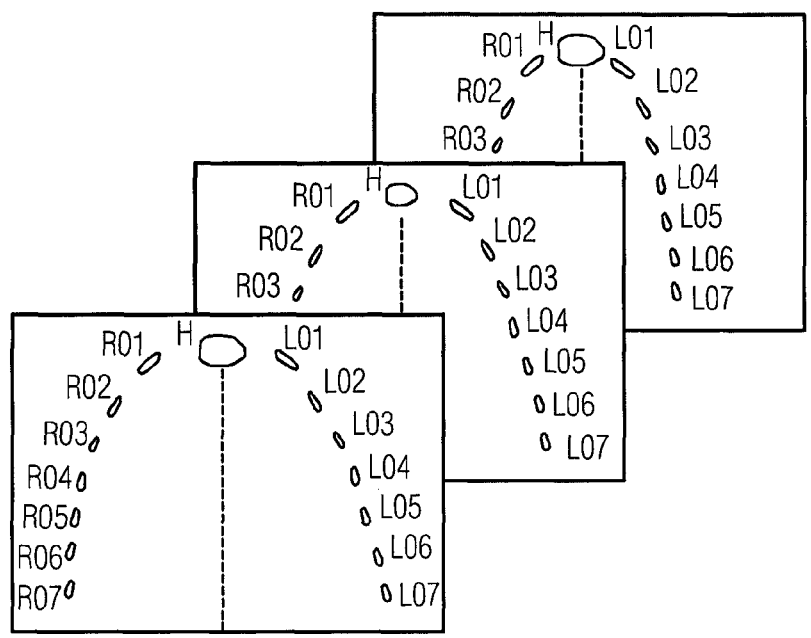
FIG. 6: shows an example labeled 2D images.

In an embodiment of the invention, the 2D images form a three-dimensional stack, wherein the position of a given anatomical label between adjacent 2D images changes based on the change of position of the cross section of the respective rib between adjacent 2D images (FIG. 6). In another embodiment of the invention the method of rib labeling comprises receiving a centerline of each of the plurality of ribs, and determining the position of the cross section of the respective rib based on the position of the centerline of the respective rib. These aspects lead to a smooth and continuous change of the positions of the anatomical labels between adjacent planes. Therefore, these aspects are particularly helpful when scrolling through a stack of labeled 2D images.

According to a further embodiment of the invention the method of rib labeling comprises displaying sequentially the 2D images forming a three-dimensional stack.

At least one embodiment of the invention can also be realized as a computation unit for rib labeling, comprising a program memory for storage of program code, the program code being present in the program memory and carrying out, when executed, receiving a plurality of two-dimensional images representing cross sections of a rib cage, each two-dimensional image comprising cross sections of a plurality of ribs, generating an anatomical label for each of the ribs in each of the two-dimensional images, each anatomical label being placed radially outside the rib cage. At least one embodiment of the invention can also be realized as medical imaging device comprising such a computation unit.

At least one embodiment of the invention can also be realized as a non-transitory computer readable medium including program segments for, when executed on a computer device, causing the computer device to carry out the inventive method. At least one embodiment of the invention can also be realized as a computer program product, comprising program code segments of a computer program stored on a non-transitory computer-readable data carrier to execute at least one embodiment of the inventive method when the computer program is executed on a computer.

At least one embodiment of the invention can also be realized as a system including a computation unit for rib labeling and a displaying unit for visualization of the rib labeling, wherein the computation unit comprises a program memory for storage of program code, the program code being present in the program memory and carrying out, when executed, receiving a plurality of two-dimensional images representing cross sections of a rib cage, each two-dimensional image comprising cross sections of a plurality of ribs, generating an anatomical label for each of the ribs in each of the two-dimensional images, each anatomical label being placed radially outside the rib cage. Such a computation unit can also be configured to obtain instructions via a user-interface. According to another embodiment of the invention, the computation unit is acting as a server and the displaying unit is acting as a client, wherein the displaying unit is configured to receive the labeled 2D image from the computation unit via a network connection.

Figure 8:
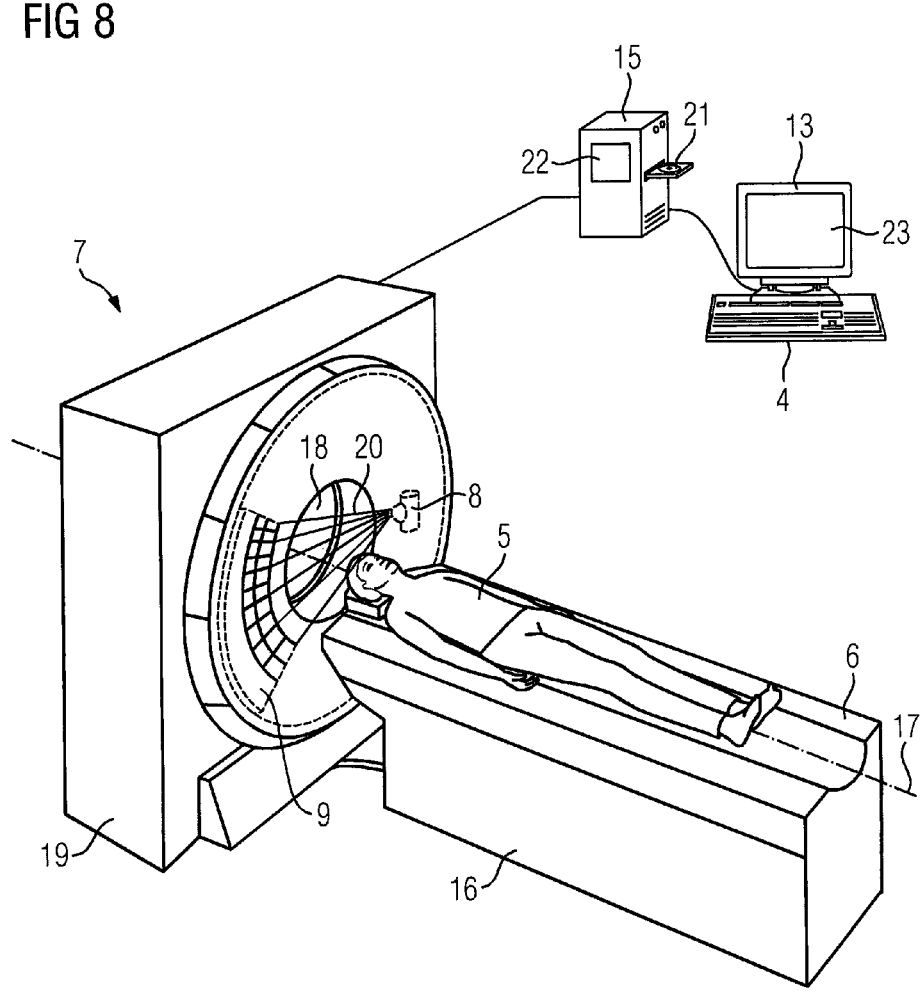
FIG. 8: shows an example embodiment of a medical imaging device with a computation unit.

FIG. 8 shows a system in connection with a computed tomography scanner 7. During the tomographic recording of an X-ray image the patient 5 lies on an examination table 6 which is connected to a table base 16 in such a way that it supports the examination table 6 with the patient 5. During a tomographic recording the examination table 6 moves the patient 5 in a spiral mode along an axis of rotation 17 through the opening 18 in the gantry 19 of the computed tomography scanner 7. During this movement a large number of projection scans of a body part of the patient 5 is created. During the tomographic recording of an X-ray image the X-ray detector 9 and the X-ray emitter 8, which cooperates with the X-ray detector 9, move about the axis of rotation 17. X-ray emitter 8 and X-ray detector 9 are arranged in a gantry 19 in such a way that they oppose one another and the X-ray beams 20 of the X-ray emitter 8 are detectable for the X-ray detector 9. The X-ray detector 9 of a computed tomography scanner 7 shown here is a detector with a plurality of rows and columns.

An X-ray detector 9 is conventionally designed as a scintillation counter in which the high-energy X-ray photons are converted by way of a scintillator into low-energy photons in the optical spectrum and then detected by way of a photodiode. Alternatively the X-ray detector 9 can be designed as a directly converting detector which converts the high-energy X-ray photons by way of a semi-conductor material directly into an electrical signal current by internal photo excitation using the photovoltaic principle. The X-ray emitter 8 is conventionally an X-ray tube. In principle other X-ray emitters 8, which are suitable for tomographic imaging, may also be used, however.

The computation unit 15 is also fitted with a program memory 22, wherein the computation unit 15 is designed to load a computer program into its internal memory. The computer program includes commands which can be read by the computation unit 15 and is itself part of a computer program product. The computer program product can by way of example be stored on a computer-readable medium 21. The commands, which can be read by the computation unit 15, of the computer program are configured to carry out the inventive method if the commands are executed on the computation unit 15.

The computer-readable medium 21 can also be by way of example a DVD, USB stick, hard drive or a diskette. The computation unit 15 is connected to a display unit 13, by way of example for graphical output of labeled 2D images 23. The display unit 13 is by way of example a (or several)

LCD, plasma, or OLED screen(s). The computation unit 15 is also connected to an input unit 4. The input unit 4 is by way of example a keyboard, mouse, what is known as a touchscreen, or a microphone for speech input.

The computation unit can comprise hardware or software. An interface enables the computation unit 15 to communicate with the X-ray tomograph. In the embodiment shown here the computation unit 15 has further interfaces in order to be able to communicate with the input unit 4 or an display unit 13. The interface is a generally known hardware or software interface, e.g. the PCI bus, USB or Firewire hardware interfaces.

Figure 7:
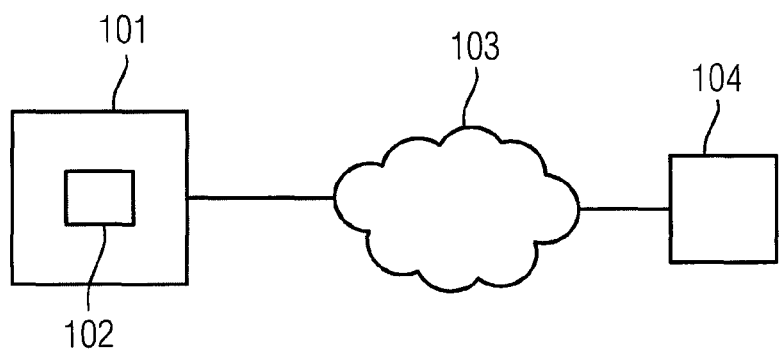
FIG. 7: shows an example embodiment of a server and client connected via a network.

FIG. 7 shows a server 101 connected over a network 103 with a client 104. The labeled 2D image can be transferred from the server 101 to the client 104 over a network 103. In this example an executable program 102 for generating the labeled 2D image is stored on the server 101. The client 104 is configured as a display unit for a graphical representation of the labeled 2D image. In further embodiments of the invention, the labeled 2D image is transferred from the server 101 over the network 103 to other units, e.g. to a Picture Archiving and Communication System (PACS).

FIG. 1 shows a flowchart of various example embodiments of the inventive method. The method comprises receiving 2D images representing cross sections of at least a part of a rib cage. These 2D images can comprise reformatted images, multiplanar reconstructions or curved planar reconstructions. An anatomical label is generated for each of the ribs in each of the two-dimensional images, each anatomical label being placed radially outside the rib cage. The term "rib cage" refers to the structure formed or enclosed by the ribs, thus the anatomical labels may overlap with other tissue such as muscle or fat. The anatomical labels do not overlap, however, with the ribs or the cross sections of the ribs in the 2D image. Each anatomical label is placed in the vicinity of a rib or its cross section. It is important, that the anatomical label allows identifying an individual rib or its cross section. The typical nomenclature for labeling ribs is given by a combination of the letter "L" for left or "R" for right in combination with a number between "01" and "12". The spine may be indicated by a "0". Other anatomical labels can be used as well, in particular other combinations of signs or letters.

An embodiment of the invention comprises identifying each rib or each cross section of a rib in a 2D image. Identifying a rib or a cross section of a rib in a 2D image may comprise automated rib ordering and pairing of ribs. In the U.S. patent application Ser. No. 13/274,515 published as US 2012/0106810 A1 the entire contents of which are hereby incorporated herein by reference, a method for automated rib ordering and pairing is disclosed.

In an embodiment of the invention, the method for rib labeling comprises receiving a centerline of each of the plurality of ribs. The centerlines are typically obtained from three-dimensional ("3D") image data. Different steps of image processing such as segmentation and rendering can be employed for extracting the centerlines based on the 3D image data by way of image processing. Typically several cross sections of different ribs appear in a 2D image due to the curved geometry of the ribs. The position of an individual cross section of a rib in the 2D image can be determined, e.g. based on the centerline of the respective rib. In an embodiment of the invention the position of the centerline in the sectional plane of the 2D image is identified with the position of the cross section of the respective rib in the 2D image.

An embodiment of the invention comprises receiving a position of a center point of the rib cage. The center point of the rib cage with respect to a 2D image can be determined by averaging the positions or the position vectors of the cross sections of all ribs represented in a 2D image. The averaging may include the weighting of the position or the position vectors of the cross section of individual ribs. The center point can be used for determining the distance between the position of the center point and of a position of a cross section of a rib. The radial placement of the anatomical labels can be realized by placing them along the direction of the distance vector. In an embodiment of the invention the position of an anatomical label depends on the absolute distance between the position of the center point and of the position of the cross section of the respective rib, e.g. by placing the label at a certain fraction of this absolute distance away from the position of the cross section of the respective rib.

In a further embodiment of the invention, a surface of the rib cage is defined, e.g. by interpolating the centerlines of the ribs. In such a case the radial placement of the anatomical labels can be realized by determining the position of the anatomical labels based on the surface of the rib cage, e.g. each anatomical label can be placed in a certain distance from the position of the cross section of the respective rib, wherein the distance vector is directed normal to the surface of the rib cage.

Figure 2:
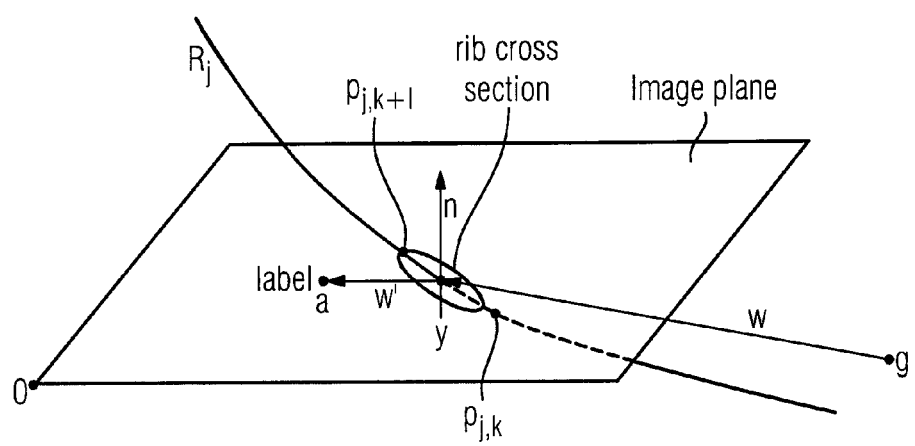
FIG. 2: shows an example schematic of the positioning of an anatomical label.

FIG. 2 shows an example schematic of the positioning of a rib label. Here the image plane of the 2D image is defined by the origin O and the normal vector n. The centerline of the j-th rib is indicated by Rj. The centerline of a rib can be based on equidistantly spaced centerline points pj,k, wherein k indicates the centerline points of the respective rib. A continuous centerline can be obtained by connecting the points through line segments or by interpolating the centerline points. In an embodiment of the invention the anatomical labels in the 2D image each line segment defined by two consecutive points pj,k and pj,k+1 is tested for intersection with the image plane. If these two consecutive points are located on different sides of the imaging plane, then the line segment defined by these two consecutive points intersects the image plane. In this case the intersection point can be obtained, e.g. via a linear equation system.

Directly placing the anatomical label over the intersection point of the respective rib would hide diagnostically relevant image information. In order to derive a more suitable position of the anatomical label a center point g of the rib cage can be derived. The center point g can be defined as the average of all rib centerline points in a given dataset. For each intersection point y between a rib centerline and an image plane a distance w=y−g can be determined. Accordingly a 3D distance vector can be determined. Such a 3D distance vector points from the center of the rib cage g radially outwards. The displacement vector can be projected into the image plane, wherein the projected distance is indicated as w'. An anatomical label can then be placed at the anchor point a=y+μw', whereby μ is a scalar value for adjusting the distance between the rib intersection point y and the anatomical label.

Figure 3:
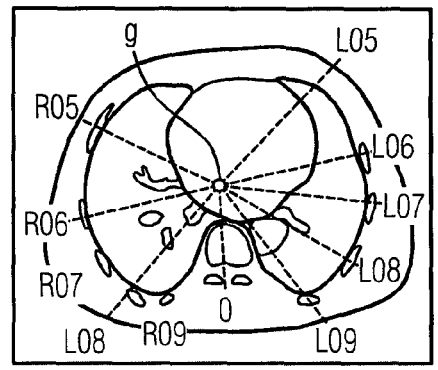
FIG. 3: shows an example labeled 2D image with a schematic indicating the position of the labels.

FIG. 3 shows an example labeled 2D image with a schematic indicating the position of the labels. The 2D image shown here is a multiplanar reconstruction with a transverse sectional plane. There are five ribs crossing the sectional plane on the right and on the left side of the rib cage. Thus these ribs also cross the image plane. They are labeled from "R05" to "R09" and "L05" to "L09", respectively. These anatomical labels are placed radially outside the rib cage. Here the radial placement is realized by placing the anatomical labels along the directions of the different distance vectors, wherein the distance vectors are given by the distance between the center point g of the rib cage and the position of the cross section of the respective rib. For some of the ribs in FIG. 3 the distance vectors are indicated by dashed lines.

Figure 4:
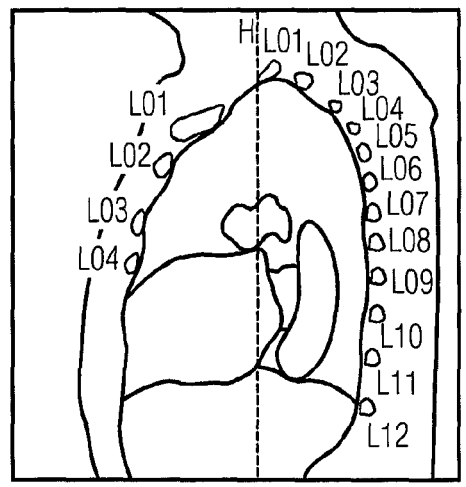
FIG. 4: shows an example labeled 2D image.
Figure 5:
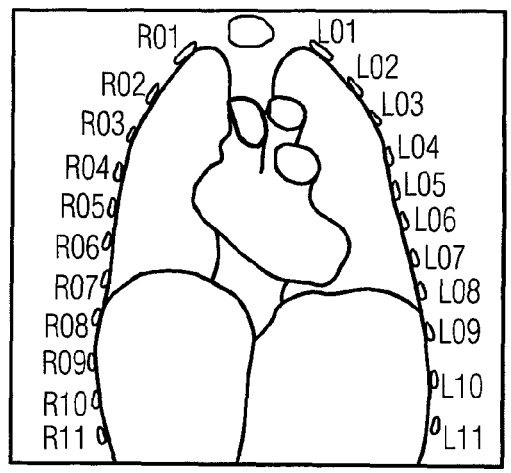
FIG. 5: shows an example labeled 2D image.

FIG. 4 shows an example labeled 2D image, the 2D image being a multiplanar reconstruction with a transverse sectional plane. FIG. 5 shows an example labeled 2D image, the 2D image being a multiplanar reconstruction with a frontal sectional plane. Each of the anatomical labels shown in FIG. 4 and FIG. 5 is placed radially outside the rib cage. In an embodiment of the invention at least two different labeled two-dimensional images are displayed simultaneously, wherein the at least two labeled 2D images differ in perspective. The different 2D images represent typically the same rib cage. E.g. FIG. 3, FIG. 4 and FIG. 5 can be displayed simultaneously, so that the 2D images differ in the orientation of the sectional planes.

Each of the 2D images shown in FIG. 3, FIG. 4 and FIG. 5 can form a part of a 3D stack. The 2D images forming a stack have typically the same orientation, e.g. the same orientation of the sectional plane. It is particularly important to achieve intuitive and reliable labeling of ribs while shifting from one image plane in a 3D stack to another image plane, e.g. by scrolling through the stack. According to an embodiment of the invention the position of a given anatomical label between adjacent 2D images in a 3D stack changes based on the change of position of the cross section of the respective rib between adjacent 2D images. As a result the position of the anatomical label between adjacent 2D images forming a 3D stack changes continuously, because the position of a rib between adjacent 2D images forming a 3D stack changes continuously. According to another aspect of the invention several 3D stacks are displayed simultaneously, so that the 2D images of different 3D stacks differ in perspective.

The difference in perspective between at least two labeled 2D images can be realized by a different viewing angle. In one embodiment of the invention a second labeled 2D image can be generated by rotating a first labeled 2D image. In such a case the viewing angle between the first and the second labeled 2D image differs. The first labeled 2D image might be given by a multiplanar reconstruction with a transverse sectional plane. A second labeled 2D image can be generated by rotating the first labeled 2D image around its vertical axis. A rotation by 90° yields a multiplanar reconstruction with a frontal sectional plane. In an embodiment of the invention a plurality of labeled 2D images with different viewing angles are generated, wherein the viewing angles are regularly spaced, e.g. equidistantly. This embodiment allows rotating the rib cage while providing a reliable and consistent labeling.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims.

Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of rib labeling, comprising
receiving, at a computer, a plurality of two-dimensional images representing cross sections of a rib cage, each two-dimensional image comprising cross sections of a plurality of ribs; the computer including a processor and a memory, wherein the processor
determines a center point of the rib cage by averaging a position or position vectors of the cross sections of all ribs represented in the two-dimensional images;
determines a distance between a position of the center point of the rib cage and a position of a cross section of a rib position; and
generates an anatomical label for each of the ribs in each of the two-dimensional images; and
places each anatomical label based on a distance between the position of the center point and a position of the cross section of the respective rib, each anatomical label being placed radially outside the rib cage.

2. The method of claim 1, wherein the processor
receives a centerline of each of the plurality of ribs, each anatomical label being placed based on a position of the centerline of the respective rib.

3. The method of claim 1, wherein the processor receives a centerline of each of the plurality of ribs, and determines the position of the cross section of the respective rib based on the position of the centerline of the respective rib.

4. The method of claim 1, wherein the processor places each anatomical label in a variable distance from the position of the cross section of the respective rib, wherein the variable distance depends on a distance between the position of the center point and the position of the cross section of the respective rib.

5. The method of claim 1, wherein the processor places each anatomical label in the same, fixed distance from the position of the cross section of the respective rib.

6. The method of claim 1, wherein the two-dimensional images are given by multiplanar reconstructions or by curved planar reconstructions.

7. The method of claim 1, further comprising:
displaying simultaneously at least two different labeled two-dimensional images, wherein the at least two labeled two-dimensional images differ in perspective.

8. The method of claim 7, wherein the at least two labeled two-dimensional images differ in the orientation of the sectional planes.

9. The method of claim 1, wherein the two-dimensional images form a three-dimensional stack, and wherein a position of a respective one of the anatomical labels between adjacent two-dimensional images changes based on a change of position of the cross section of the respective rib between adjacent two-dimensional images.

10. The method of claim 9, wherein the processor receives a centerline of each of the plurality of ribs, and determines the position of the cross section of a respective rib based on the position of the centerline of the respective rib.

11. The method of claim 9, further comprising:
displaying sequentially the two-dimensional images forming a three-dimensional stack.

12. A computer configured to label ribs of a rib cage, the computer comprising:
a processor; and
a program memory configured to store program code, the program code being present in the program memory and being capable of carrying out, when executed by the processor,
receiving a plurality of two-dimensional images representing cross sections of the rib cage, each two-dimensional image comprising cross sections of a plurality of ribs,
determining a center point of the rib cage by averaging a position or position vectors of the cross sections of all ribs represented in the two-dimensional images;
determining a distance between a position of the center point of the rib cage and a position of a cross section of a rib position;
generating an anatomical label for each of the ribs in each of the two-dimensional images; and
placing each anatomical label based on a distance between the position of the center point and a position of the cross section of the respective rib, each anatomical label being placed radially outside the rib cage.

13. A medical imaging device comprising the computer of claim 12.

14. A non-transitory computer readable medium including program segments for, when executed on a computer device, causing the computer device to carry out the method of claim 1.

15. A computer program product, comprising program code segments of a computer program stored on a non-transitory computer-readable data carrier to execute the method of claim 1 when the computer program is executed on a computer.

16. A system comprising:
a computer configured to label ribs of a rib cage in an image; and
a display configured to display the rib labeling, wherein the computer comprises a processor and a program memory configured to store program code, the program code being present in the program memory and being configured to carry out, when executed, by the processor,
receiving a plurality of two-dimensional images representing cross sections of the rib cage, each two-dimensional image comprising cross sections of a plurality of ribs,
determining a center point of the rib cage by averaging a position or position vectors of the cross sections of all ribs represented in the two-dimensional images;
determining a distance between a position of the center point of the rib cage and a position of a cross section of a rib position;
generating an anatomical label for each of the ribs in each of the two-dimensional images, and
placing each anatomical label based on a distance between the position of the center point and a position of the cross section of the respective rib, each anatomical label being placed radially outside the rib cage, wherein the display is configured to receive the labeled two-dimensional images from the computer and wherein the display is further configured to display the labeled two-dimensional images.

17. The system of claim 16, wherein the computer is configured to obtain instructions via a user-interface.

18. The system of claim 16, wherein the computer is configured to act as a server and the display is configured to act as a client, and wherein the display is configured to receive the labeled two-dimensional images from the computer via a network connection.

* * * * *